(12) United States Patent
Schulz et al.

(10) Patent No.: US 11,623,912 B2
(45) Date of Patent: Apr. 11, 2023

(54) TRIESTERS OF CYCLOHEXANETRIPROPIONIC ACID

(71) Applicant: Evonik Operations GmbH, Essen (DE)

(72) Inventors: Imke Schulz, Lüdinghausen (DE); Michael Grass, Haltern am See (DE); Robert Franke, Marl (DE); Johannes Kraft, Marl (DE); Matthias Beller, Ostseebad Nienhagen (DE); Ralf Jackstell, Rostock (DE)

(73) Assignee: Evonik Operations GmbH, Essen (DE)

( * ) Notice: Subject to any disclaimer, the term of this patent is extended or adjusted under 35 U.S.C. 154(b) by 29 days.

(21) Appl. No.: 17/113,449

(22) Filed: Dec. 7, 2020

(65) Prior Publication Data

US 2021/0179534 A1 Jun. 17, 2021

(30) Foreign Application Priority Data

Dec. 17, 2019 (EP) ..................................... 19216888

(51) Int. Cl.
*C07C 69/753* (2006.01)
*C07C 67/38* (2006.01)
*C08F 14/06* (2006.01)
*C08K 5/12* (2006.01)

(52) U.S. Cl.
CPC ............ *C07C 69/753* (2013.01); *C07C 67/38* (2013.01); *C08F 14/06* (2013.01); *C08K 5/12* (2013.01)

(58) Field of Classification Search
CPC ........ C08K 5/12; C08K 5/098; C08K 5/0016; C08K 2201/014; C08K 5/11; C08L 27/06; C08L 5/12; C08L 91/00; C09D 127/06; C09D 7/63; C07C 67/02; C07C 69/608; C07C 2601/14; C07C 67/38; C07C 69/753; C07C 2601/08; C07C 69/00; C07C 67/00; C08F 14/06; C08J 2327/06; C08J 5/18

See application file for complete search history.

(56) References Cited

U.S. PATENT DOCUMENTS 5,153,354 A * 10/1992 Schroder ................. C07C 67/38
560/114
2007/0123716 A1 5/2007 Okoshi
2018/0319954 A1 11/2018 Woldt et al.

OTHER PUBLICATIONS

European Search Report dated Jun. 23, 2020 in EP 19216888.8 (5 pages).

* cited by examiner

*Primary Examiner* — Yevgeny Valenrod
*Assistant Examiner* — Blaine G Doletski
(74) *Attorney, Agent, or Firm* — Taylor English Duma LLP; Philip P. McCann

(57) ABSTRACT

The invention relates to triesters of cyclohexanetripropionic acid, preparation thereof and use thereof as plasticizers for polymers wherein examples of the triester of cyclohexanetripropionic acid include tri($^n$butyl) cyclohexane-1,2,4-tripropionate, tri(methylpropyl) cyclohexane-1,2,4-tripropionate, tri($^n$pentyl) cyclohexane-1,2,4-tripropionate, tri($^{iso}$pentyl) cyclohexane-1,2,4-tripropionate, tri(2-methylbutyl) cyclohexane-1,2,4-tripropionate, tri(3-methylbutyl) cyclohexane-1,2,4-tripropionate, tri($^n$hexyl) cyclohexane-1,2,4-tripropionate, tri($^{iso}$hexyl) cyclohexane-1,2,4-tripropionate, tri($^n$heptyl) cyclohexane-1,2,4-tripropionate, tri($^{iso}$heptyl) cyclohexane-1,2,4-tripropionate, tri($^n$octyl) cyclohexane-1,2,4-tripropionate, tri($^{iso}$octyl) cyclohexane-1,2,4-tripropionate, tri(2-ethylhexyl) cyclohexane-1,2,4-tripropionate, tri($^n$nonyl) cyclohexane-1,2,4-tripropionate, tri($^{iso}$nonyl) cyclohexane-1,2,4-tripropionate, tri($^n$decyl) cyclohexane-1,2,4-tripropionate, tri($^{iso}$decyl) cyclohexane-1,2,4-tripropionate, and tri(2-propylheptyl) cyclohexane-1,2,4-tripropionate.

14 Claims, No Drawings

TRIESTERS OF CYCLOHEXANETRIPROPIONIC ACID

CROSS REFERENCE TO RELATED APPLICATIONS

This application is a 35 U.S.C. § 119 patent application which claims the benefit of European Application No. 19216888.8 filed Dec. 17, 2019, which is incorporated herein by reference in its entirety.

FIELD

The present invention relates to triesters of cyclohexanetripropionic acid, to preparation and use thereof as plasticizers for polymers.

BACKGROUND

To improve the processability and also for adjusting application-relevant properties to the respective requirements, polymer plasticizers are added. To achieve the particular desired properties here, plasticizers having various effect profiles are available. Compounds from the group of phthalates belong to the most important plasticizers for PVC and vinyl chloride-containing copolymers.

Depending on factors including the number of carbons in the alcohol moieties of the ester functions, phthalates have different properties and are suitable accordingly to a greater or lesser extent for different plasticizer applications. Whereas phthalates having short-chain alcohol moieties, for example dibutyl phthalates and dipentyl phthalates, have a low and therefore advantageous gelation temperature and are thus used as fast gellers, these phthalates are unsuitable for other applications due to their high volatility. Phthalates having longer chain alcohol moieties, for example di$^{iso}$nonyl phthalate (DINP), do indeed have poorer gelling properties than the lighter homologues but at the same time profit from a lower volatility, but which is still too high for certain applications which have to tolerate high temperatures. Even the relatively low volatility of di(tridecyl) phthalate is not low enough to allow use of this phthalate in many high temperature applications. Since phthalates having more than 13 carbon atoms in the alcohol moiety have low polymer compatibility and the corresponding polymer phthalate mixtures tend to separate, there are no representatives from the group of phthalate plasticizers having more than 13 carbon atoms in the alcohol moiety which could be used as plasticizer, for example, in high temperature cables.

Owing to their lower volatility compared to phthalates, plasticizers from the group of trimellitates are used for high temperature applications. The text book "Plasticizers—Principles and Practice" by A. S. Wilson (The Institute of Materials, 1995, pages 166 to 170) describes trimellitates having alcohol moieties comprising 7 to 9 carbon atoms or mixtures of C6- and C8-esters or C7-, C8- and C9-esters of trimellitic acid as commercially interesting, in which tri(2-ethylhexyl) trimellitate is emphasized as the most important trimellitate. Even these trimellitates are often still too volatile for use in high temperature cables.

The published specification US 2018/0319954 A1 discloses trimellitates and alongside this also cyclohexane-1,2,4-tricarboxylates and their suitability as plasticizers.

SUMMARY

The object of the present invention is now to provide a novel group of plasticizers, representatives of which cover a broad range of properties, that is to say, which can be used for many different applications. This novel plasticizer group should preferably comprise agents having very good gelling capability and agents having excellent high temperature properties. Representatives of the novel plasticizer group should preferably be superior to the trimellitates in high temperature applications such as cables.

This object is achieved by triesters of cyclohexanetripropionic acid. The present invention relates to triesters of cyclohexanetripropionic acid, in which the three alcohol moieties of the three ester groups each comprise 2, 3, 4, 5, 6, 7, 8, 9, 10, 11 or 12 carbon atoms.

DETAILED DESCRIPTION

Triesters of cyclohexanetripropionic acid, as all carboxylic esters, are formed formally from carboxylic acid and alcohol, whereby the ester comprises an acid moiety and an alcohol moiety. Triesters of cyclohexanetripropionic acid according to the invention are composed of the cyclohexanetripropionic acid moiety and three alcohol moieties. These alcohol moieties each comprise 2, 3, 4, 5, 6, 7, 8, 9, 10, 11 or 12 carbon atoms.

Triesters of cyclohexanetripropionic acid according to the invention are also referred to below in abbreviated form as triesters according to the invention.

Surprisingly, it has been found that representatives of this novel plasticizer group are suitable for plastisol applications, have a low gelation temperature and may be used advantageously as fast gellers, whereas other representatives of this group can advantageously be used in thermoplastic applications. In plastisol and in thermoplastic applications, representatives of this plasticizer group have a low mass loss. Good low temperature flexibility (low glass transition temperature) can also be attained with representatives of this group.

In addition to the desired suitability of representatives of the novel plasticizer group for high temperature applications, there are representatives in the group which in plastisol applications enable a low viscosity together with advantageous thickening characteristics of the plastisol in question.

The three propionic ester radicals of the esters according to the invention can be bonded to various positions of the cyclohexane ring. However, the triesters according to the invention are preferably triesters of cyclohexane-1,2,4-tripropionic acid or triesters of cyclohexane-1,3,5-tripropionic acid, especially triesters of cyclohexane-1,2,4-tripropionic acid.

The alcohol moieties of the triesters of cyclohexanetripropionic acid may be cyclic or acyclic alkyl radicals with or without functional groups including multiple bonds. Here, it is irrelevant whether the functional groups originate from the alcohol used for preparing the triesters according to the invention or were subsequently inserted into the triester molecule. Also possible are alcohol moieties comprising aromatic rings which in turn bear no, or one or more, functional groups. The alcohol moieties of the triesters according to the invention, besides the oxygen of the ester function, preferably do not comprise any other heteroatoms and contain no multiple bonds.

These alcohol moieties, based formally on alkanols, preferably on acyclic alkanols, have the advantage that the preparation of the resulting triesters is possible at particularly low cost owing to the availability of the alkanols.

The present invention relates preferably to triesters of cyclohexanetripropionic acid, in which the three alcohol moieties of the three ester groups each comprise 2 to 9, preferably 4 to 9 or 4, 5, 6, 7, 8 or 9 carbon atoms. These triesters have good gelling properties and the plastisols prepared using them are characterized by low plastisol viscosity which also increases only marginally over time. In plastisol applications, for example composed of films, only a small loss of mass occurs in air. As evident from the low glass transition temperatures, the low temperature flexibility of test specimens comprising these triesters is higher than in the case of comparative compounds. However, the triesters according to the invention are preferably triesters of cyclohexane-1,2,4-tripropionic acid or triesters of cyclohexane-1,3,5-tripropionic acid, particularly triesters of cyclohexane-1,2,4-tripropionic acid, the alcohol moieties of which preferably formally originate from an acyclic alkanol.

The present invention also preferably relates to triesters of cyclohexanetripropionic acid, in which the three alcohol moieties of the three ester groups each comprise 7 to 12, preferably 8 to 10 and especially 8 or 9 carbon atoms. These triesters are characterized by a very low mass loss at elevated temperatures and are therefore highly suited for high temperature applications. In addition, the low temperature flexibility of test specimens comprising these triesters is higher than in the case of comparative compounds. However, the triesters according to the invention are preferably triesters of cyclohexane-1,2,4-tripropionic acid or triesters of cyclohexane-1,3,5-tripropionic acid, particularly triesters of cyclohexane-1,2,4-tripropionic acid, the alcohol moieties of which preferably formally originate from an acyclic alkanol.

Triesters according to the invention preferably comprise two or three alcohol moieties having identical empirical formula within one molecule. In this case, the "empirical formula identical" alcohol moieties within one triester have the same arrangement of atoms present, or differ in structure, i.e. are isomeric alcohol moieties. Preferably, all alcohol moieties present in one molecule of the triesters according to the invention have identical empirical formulae and at the same time identical or different structural formulae. Triesters according to the invention, of which the alcohol moieties have identical empirical formulae and different structural formulae, comprise isomeric alcohol radicals. Such triesters are also advantageously liquid at low temperatures.

Preferred triesters of cyclohexanetripropionic acid, i.e. triesters of cyclohexane-1,2,4-tripropionic acid, have the structure reproduced in formula I, wherein the radicals R have identical empirical formulae and at the same time identical or different structural formulae.

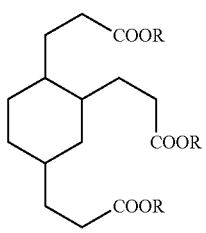

Formula I

In one embodiment, the radicals R of the formula I are acyclic alkyl radicals having 2 to 8 or 9, particularly having 4, 5, 6 or 7 carbon atoms. In another embodiment, the radicals R of the formula I are acyclic alkyl radicals having 7 to 10, particularly having 8 or 9 carbon atoms.

The present invention further relates to mixtures of at least two triesters of cyclohexanetripropionic acid according to the invention. In this case, the at least two triesters according to the invention may differ in their empirical formulae, in their structural formulae or in both. An example of a mixture in which there is a difference in the empirical formula and the mixture comprises at least two triesters according to the invention is a mixture comprising tri("pentyl) cyclohexane-1,2,4-tripropionate and tri(2-ethylhexyl) cyclohexane-1,2,4-tripropionate. If the at least 2 esters according to the invention differ in their structural formula, at least one triester of cyclohexane-1,2,4-tripropionic acid and at least one triester of cyclohexane-1,3,5-tripropionic acid, for example, may be present in the mixture. Alternatively or in addition to possible differences in the position of the propionic ester radicals on the cyclohexane ring, the mixture may comprise at least two triesters according to the invention which comprise "empirical formula identical" alcohol moieties of different structure, i.e. isomeric alcohol moieties. For example, a mixture may comprise one triester according to the invention of which the alcohol moieties are invariably linear and comprise one triester according to the invention of which the alcohol moieties are uniformly branched. An example of one such mixture is the combination of tri("pentyl) cyclohexane-1,2,4-tripropionate and tri(2-methylbutyl) cyclohexane-1,2,4-tripropionate. Also possible are more complex mixtures comprising tri("butyl) cyclohexane-1,2,4-tripropionate, tri($^{iso}$pentyl) cyclohexane-1,2,4-tripropionate, tri("butyl) cyclohexane-1,3,5-tripropionate and tri($^{iso}$pentyl) cyclohexane-1,3,5-tripropionate.

The prefix "iso" marks the fact that this is an isomer mixture with a common number of carbons. An $^{iso}$pentyl radical thus comprises at least two isomeric alkyl radicals having 5 carbon atoms, in which in this designation there is no information on how many and which isomeric radicals are present in which ratio. When identical triesters according to the invention are not exclusively present in an isomeric mixture of tri($^{iso}$alkyl) cyclohexanetripropionate, it is accordingly a mixture of at least two triesters according to the invention which differ in their structural formulae.

Preferred triesters according to the invention or mixtures according to the invention are tri("butyl) cyclohexane-1,2,4-tripropionate, tri(methylpropyl) cyclohexane-1,2,4-tripropionate, tri("pentyl) cyclohexane-1,2,4-tripropionate, tri($^{iso}$pentyl) cyclohexane-1,2,4-tripropionate, tri(2-methylbutyl) cyclohexane-1,2,4-tripropionate, tri(3-methylbutyl) cyclohexane-1,2,4-tripropionate, tri("hexyl) cyclohexane-1,2,4-tripropionate, tri($^{iso}$hexyl) cyclohexane-1,2,4-tripropionate, tri("heptyl) cyclohexane-1,2,4-tripropionate, tri($^{iso}$heptyl) cyclohexane-1,2,4-tripropionate, tri("octyl) cyclohexane-1,2,4-tripropionate, tri($^{iso}$octyl) cyclohexane-1,2,4-tripropionate, tri(2-ethylhexyl) cyclohexane-1,2,4-tripropionate, tri("nonyl) cyclohexane-1,2,4-tripropionate, tri($^{iso}$nonyl) cyclohexane-1,2,4-tripropionate, tri("decyl) cyclohexane-1,2,4-tripropionate, tri($^{iso}$decyl) cyclohexane-1,2,4-tripropionate, tri(2-propylheptyl) cyclohexane-1,2,4-tripropionate, tri("butyl) cyclohexane-1,3,5-tripropionate, tri(methylpropyl) cyclohexane-1,3,5-tripropionate, tri("pentyl) cyclohexane-1,3,5-tripropionate, tri($^{iso}$pentyl) cyclohexane-1,3,5-tripropionate, tri(2-methylbutyl) cyclohexane-1,3,5-tripropionate, tri(3-methylbutyl) cyclohexane-1,3,5-tripropionate, tri("hexyl) cyclohexane-1,3,5-tripropionate, tri(isohexyl) cyclohexane-1,3,5-tripropionate, tri("heptyl) cyclohexane-1,3,5-tripropionate, tri(isoheptyl) cyclohexane-1,3,5-tripropionate, tri("octyl) cyclohexane-1,3,5-tripropionate, tri(isooctyl) cyclohexane-1,3,5-tripropionate, tri(2-ethylhexyl) cyclohexane-1,3,5-tripropionate, tri("nonyl) cyclohexane-1,3,5-tripropionate, tri(isononyl) cyclohexane-1,3,5-tripropionate, tri("decyl) cyclohexane-1,3,5-tripropionate, tri(isodecyl) cyclohexane-1,3,5-tripropionate and tri(2-propylheptyl) cyclohexane-1,3,5-tripropionate.

As already described, esters according to the invention have advantageous properties when used as plasticizer for polymers. The present invention therefore further relates to a plasticizer for polymers comprising a triester according to the invention or a mixture according to the invention (comprising at least two of these triesters) and optionally at least one further polymer-plasticizing compound. This plasticizer is particularly well suited for PVC.

The present invention also relates to a composition comprising a triester according to the invention or a mixture according to the invention (comprising at least two of these triesters) or a plasticizer according to the invention and one or more polymers.

Suitable polymers are preferably selected from the group consisting of polyvinyl chloride (PVC), homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atoms, acrylonitrile or cyclic olefins, polyvinylidene chloride (PVDC), polyacrylates, especially polymethyl methacrylate (PMMA), polyalkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphide (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

In a preferred embodiment, at least one polymer or preferably at least 90% by weight of the polymers in the composition is/are selected from the group consisting of polyvinyl chloride (PVC), polyalkyl methacrylate (PAMA), polyvinyl butyral (PVB), polyurethane, polysulfide, polylactic acid (PLA), polyhydroxybutyral (PHB), nitrocellulose and copolymers of vinyl chloride with vinyl acetate or with butyl acrylate.

The amount of triester according to the invention in the composition according to the invention comprising one or more polymers is preferably 5 to 150 parts by mass, preferably 10 to 120 parts by mass, particularly preferably 15 to 110 parts by mass and especially preferably 20 to 100 parts by mass per 100 parts by mass of polymer. However, compositions comprising one or more polymers are also conceivable comprising less than 20 parts by mass of triester according to the invention per 100 parts by mass of polymer.

The composition according to the invention is with preference a constituent of an adhesive, of a sealing compound, of a coating composition, of a lacquer, of a paint, of a plastisol, of a dryblend, of a foam, of a synthetic leather, of a floor covering, particularly the top layer or foam layer thereof, of a roofing membrane, of an underbody protection, of a fabric coating, of a cable, of a wire insulation, of a hose, of an extruded or injection moulded article, of a film, of an article in the automotive interior sector, of a wallpaper, of an ink, of a toy, of a contact sheet, of a food packaging or of a medical article, especially of a tube or of a blood bag.

The present invention further relates to the use of a triester according to the invention or a mixture according to the invention (comprising at least two of these triesters) as plasticizer for polymers. The triester according to the invention or the mixture according to the invention (comprising at least two of these triesters) is preferably used as plasticizer for the polymers already mentioned above, particularly for polyvinyl chloride (PVC), polyalkyl methacrylate (PAMA), polyvinyl butyral (PVB), polyurethane, polysulfide, polylactic acid (PLA), polyhydroxybutyral (PHB), nitrocellulose and copolymers of vinyl chloride with vinyl acetate or with butyl acrylate. Particular preference is given to the use as plasticizer for polyvinyl chloride (PVC).

This use results with preference in the utilization of a triester according to the invention or a mixture according to the invention (comprising at least two of these triesters) in adhesives, sealing compounds, coating compositions, lacquers, paints, plastisols, foams, synthetic leathers, floor coverings, particularly top layer or foam layer, roofing membranes, underbody protection, fabric coatings, cables, wire insulation, hoses, extruded articles, films, in the automotive interior sector, in wallpapers, inks, toys, contact sheets, food packaging or medical articles, especially in tubes or blood bags.

In a preferred embodiment, triesters of cyclohexanetripropionic acid, in which the three alcohol moieties of the three ester groups comprise 7 to 12, preferably 8 to 10 and especially 8 or 9 carbon atoms, are used as polymer-plasticizing compound in high temperature applications, especially in high temperature cables or dashboard components.

In another preferred embodiment, triesters of cyclohexanetripropionic acid, in which the three alcohol moieties of the three ester groups comprise 2 to 9, preferably 4 to 9 or 4, 5, 6, 7, 8 or 9 carbon atoms, are used as polymer-plasticizing compound in plastisol applications. Preference is given to use in fabric coatings, wallpapers, synthetic leathers and in films, roof membranes and floor coverings.

The triesters according to the invention can be prepared by
 ring hydrogenation of the corresponding triester of benzenetripropionic acid,
 transesterification of the trialkyl ester of the cyclohexanetripropionic acid with at least one alcohol comprising 2, 3, 4, 5, 6, 7, 8, 9, 10, 11 or 12 carbon atoms, wherein the alcohol of the alcohol moiety of the trialkyl ester to be incorporated is higher boiling than the alcohol of the alcohol moiety which is to be replaced in the context of the transesterification,
 esterification of cyclohexanetripropionic acid with at least one alcohol comprising 2, 3, 4, 5, 6, 7, 8, 9, 10, 11 or 12 carbon atoms or
 alkoxycarbonylation of trivinylcyclohexane with at least one alcohol comprising 2, 3, 4, 5, 6, 7, 8, 9, 10, 11 or 12 carbon atoms.

With preference, the trimethyl ester or the triethyl ester is used in the transesterification.

The present application relates by way of preference to the preparation of triesters of cyclohexanetripropionic acid according to the invention by ring hydrogenation of triesters of benzenetripropionic acid, in which the alcohol moieties of the ester groups each comprise 2, 3, 4, 5, 6, 7, 8, 9, 10, 11 or 12 carbon atoms, transesterification of the trialkyl ester of the cyclohexanetripropionic acid with at least one alcohol comprising 2, 3, 4, 5, 6, 7, 8, 9, 10, 11 or 12 carbon atoms, wherein the alcohol of the alcohol moiety of the trialkyl ester to be incorporated is higher boiling than the alcohol of the alcohol moiety which is to be replaced in the context of the transesterification, by esterification of cyclohexanetripropionic acid with at least one alcohol comprising 2, 3, 4, 5, 6, 7, 8, 9, 10, 11 or 12 carbon atoms or by alkoxycarbonylation of trivinylcyclohexane with at least one alcohol comprising 2, 3, 4, 5, 6, 7, 8, 9, 10, 11 or 12 carbon atoms.

Particular preference is given to the preparation of the triesters of cyclohexane-1,2,4-tripropionic acid using the respective cyclohexane-1,2,4 compounds.

With preference, the trimethyl ester or the triethyl ester is used in the transesterification.

The present invention particularly preferably relates to the preparation of triesters of cyclohexane-1,2,4-tripropionic acid according to the invention by ring hydrogenation of triesters of benzene-1,2,4-tripropionic acid, in which the alcohol moieties of the ester groups each comprise 2, 3, 4, 5, 6, 7, 8, 9, 10, 11 or 12 carbon atoms, by transesterification of the trimethyl ester or the triethyl ester of cyclohexane-1,2,4-tripropionic acid with at least one alcohol comprising 2, 3, 4, 5, 6, 7, 8, 9, 10, 11 or 12 carbon atoms, by esterification of cyclohexane-1,2,4-tripropionic acid with at least one alcohol comprising 2, 3, 4, 5, 6, 7, 8, 9, 10, 11 or 12 carbon atoms or by alkoxycarbonylation of 1,2,4-trivinylcyclohexane with at least one alcohol comprising 2, 3, 4, 5, 6, 7, 8, 9, 10, 11 or 12 carbon atoms.

The ring hydrogenation of the triesters of benzene-1,2,4-tripropionic acid to give the triesters according to the invention can be carried out in one or more hydrogenation units connected in series. The hydrogenation units preferably each consist of at least one, preferably two or more hydrogenation reactor(s). This at least one hydrogenation reactor may be a tubular reactor, tube bundle reactor or preferably a shaft oven. The individual reactors can be operated adiabatically, polytropically or practically isothermally, i.e. with a temperature increase of typically less than 10° C. In this case in particular, the reactors operated in loop mode are quasi-isothermally driven, preferably operated with a temperature increase of less than 10° C., particularly preferably less than 5° C. One or more of the hydrogenation units can be operated in loop mode.

The hydrogenation of the triesters of benzenetripropionic acid is preferably carried out continually with a hydrogen-containing gas on solid catalysts arranged in a fixed bed.

The hydrogenation gases used can be any hydrogen-containing gas mixtures which do not contain any harmful amounts of catalyst poisons such as carbon monoxide or hydrogen sulfide. The use of inert gases is optional, hydrogen preferably being used at a purity of greater than 95%, especially greater than 98%. Inert gas fractions can be, for example, nitrogen or methane.

With preference, solid hydrogenation catalysts are used comprising at least one metal of transition group eight of the Periodic Table of the Elements. The active metals of transition group eight of the Periodic Table of the Elements used are preferably platinum, rhodium, palladium, cobalt, nickel or ruthenium or a mixture of two or more thereof, with particular preference being given to ruthenium as active metal. In addition to the metals already mentioned, at least one metal of transition group one and/or seven of the Periodic Table of the Elements can additionally be present in the catalysts. Preference is given to using rhenium and/or copper. The catalysts used are preferably supported catalysts. Examples of supports that can be used include the following substances: activated carbon, silicon carbide, aluminium oxide, silicon oxide, aluminosilicate, titanium dioxide, zirconium dioxide, magnesium oxide and/or zinc oxide or mixtures thereof. Particular preference is given to using a catalyst having an aluminium oxide or a titanium dioxide support. In addition, these support materials may comprise alkali metals, alkaline earth metals and/or sulfur. Preference is given to using ruthenium catalysts.

The hydrogenation process is preferably carried out in cocurrent in a liquid/gas mixed phase or liquid phase in triphasic reactors, in which the hydrogenation gas is distributed in the liquid reactant/product stream in a manner known per se. In the interests of a uniform liquid distribution, of improved removal of heat of reaction and/or of a high space-time yield, the reactors operated in loop mode are preferably operated with high liquid loadings of 10 to 400, preferably of 20 to 200 and particularly preferably of 40 to 150 m$^3$ per m$^2$ of cross section of the empty reactor and per hour.

The hydrogenation can be conducted in the absence or preferably in the presence of a solvent. The solvents used can be all liquids which form a homogeneous solution with the reactant and product, are inert under hydrogenation conditions and can be easily removed from the product. The solvent may also be a mixture of two or more substances and optionally comprise water. Most preferably, the product of the hydrogenation is used as solvent.

Both the transesterification of the trimethyl ester of cyclohexanetripropionic acid with at least one alcohol comprising 2, 3, 4, 5, 6, 7, 8, 9, 10, 11 or 12 carbon atoms and the esterification of cyclohexanetripropionic acid with one or more such alcohols is preferably carried out in the presence of a catalyst or two or more catalysts, for example using Brönstedt acids or bases or Lewis acids or bases as catalyst. Particularly suitable catalysts have been found to be sulfuric acid, methanesulfonic acid, p-toluenesulfonic acid, metals or compounds thereof. Examples of particularly preferred metal catalysts are tin powders, tin(II) oxide, tin(II) oxalate, titanic esters such as tetraisopropyl orthotitanate or tetrabutyl orthotitanate, and also zirconium esters such as tetrabutyl zirconate, and also sodium methoxide and potassium methoxide. The cyclohexanetripropionic acid is accessible via hydroxycarbonylation, i.e. the noble metal-catalyzed reaction of trivinylcyclohexane with CO and $H_2O$.

The esterification and transesterification process can be carried out in typical esterification apparatus, known to those skilled in the art, under customary process conditions. The process takes place preferably at temperatures at or above the boiling point of the alcohol formed in the reaction so that this can be distilled off from the reaction mixture. Examples of suitable transesterification processes are described in the experimental section.

The esterification process or the transesterification process is preferably carried out at a temperature of 100 to 300°

C., preferably at 120 to 270° C. and especially at 140 to 250° C. The pressure within the esterifcation apparatus is preferably 0.1 to 20 or 15 bar, particularly 0.1 to 10 bar.

Preference is given to an alkoxycarbonylation process comprising the process steps of:

a) initially charging one of the compounds (i), (ii), (iii) or a mixture of at least two of these compounds;

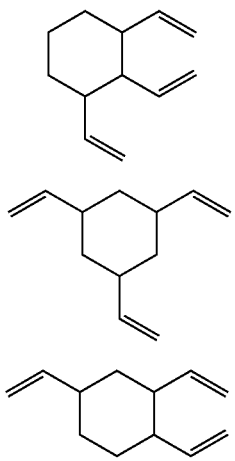

b) adding the ligand (L) and a compound comprising Pd or a complex comprising Pd and the ligand (L);

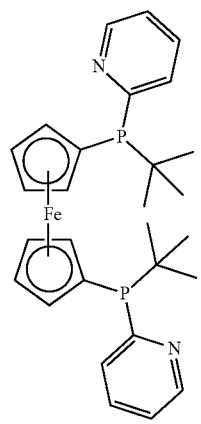

c) adding an alcohol having 1 to 12 carbon atoms;
d) feeding in CO;
e) heating the reaction mixture of a) to d), wherein the compound/the mixture of a) is converted to a triester.

In one variant of the process, the compound (1) is initially charged in process step a) and in another variant the compound (ii). The alcohol in process step c), besides the oxygen, preferably does not comprise any further heteroatoms and contains no multiple bonds and is selected in particular from methanol, ethanol, "butanol, methylpropanol, "pentanol, $^{iso}$pentanol, 2-methylbutanol, 3-methylbutanol, "hexanol, $^{iso}$hexanol, "heptanol, $^{iso}$heptanol, "octanol, $^{iso}$octanol, 2-ethylhexanol, "nonanol, $^{iso}$nonanol, "decanol, $^{iso}$decanol and 2-propylheptanol.

Particular preference is given to preparing the trimethyl ester by methoxycarbonylation and this is then transesterified to the triester according to the invention or to the mixture of triesters according to the invention.

In the alkoxycarbonylation, CO is added in process step d) preferably up to a pressure in the range of 20 bar to 60 bar and particularly at 30 bar to 50 bar. The temperature in process step e) is preferably in the range of 90° C. to 130° C., particularly in the range of 100° C. to 120° C.

Following the alkoxycarbonylation, the triester is preferably purified in a step f).

Experimental Section:

Acid Number:

The acid number was determined in accordance with DIN EN ISO 2114.

Gc Analyses:

The GC analysis took place with the following parameters:

Capillary column: 30 m DB5; 0.25 mm ID; 0.25 μm film
Carrier gas: Helium
Column pressure:
Split: about 23.8 ml/min
Oven temperature programme (duration: 50° C. (for 1 min), heating at 7.5° C./min to 350° C. (hold temperature for 30 min)
Injector: 350° C.
Detector (FID): 400° C.
Injection volume: 1.0 μl Components in the sample chromatogram were identified using a comparative solution of the relevant esters. This was followed by standardization of the signals in the sample chromatogram to 100 area %. The molar ratios were determined in sufficient approximation from the area ratios of the individual signals.

The purity was determined via the fraction of the product signals as a proportion of the total areas in the chromatogram.

Example 0: Preparation of Trimethyl Cyclohexane-1,2,4-Tripropionate

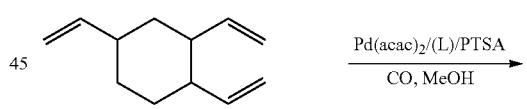

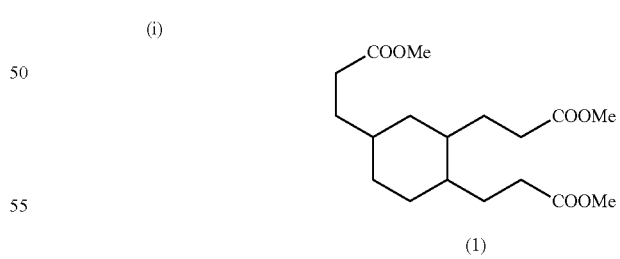

[Pd(acac)$_2$] (15.2 mg, 0.1 mol %), (L) (see formula above, 103 mg, 0.4 mol %) and paratoluenesulfonic acid (PTSA, 143 mg, 1.5 mol %) were placed in a 100 ml steel autoclave under an argon atmosphere. Then, methanol (MeOH, 30 ml) and trivinylcyclohexane (1) (8.1 g, 50 mmol) were injected by syringe. The autoclave was flushed three times with CO and then pressurized at a CO pressure of 40 bar. The reaction was carried out at 110° C. for 10 h. Then, the autoclave was cooled to room temperature and depressurized. The desired product was purified by distillation (165° C. at 10⁻³ bar) and characterized by ¹H-, ¹³C-NMR and HR-MS (15.6 g, yield 91%, purity 98%).

¹H-NMR (300 MHz, $C_6D_6$) δ=3.39-3.37 (m, 9H), 2.24-1.86 (m, 7H), 1.48-0.27 (m, 14H). ¹³C-NMR (75 MHz, $C_6D_6$) δ=173.68-173.54 (m), 51.04, 40.60-40.47 (m), 38.24, 38.14, 37.51, 37.07, 36.54, 36.10, 35.52, 35.14, 33.87, 32.70, 32.55, 32.51, 32.38, 32.29, 32.23, 32.08, 31.97, 31.86, 31.76, 31.68, 31.63, 31.43, 30.98, 30.79, 30.75, 29.31, 28.52, 28.47, 28.34, 28.13, 28.11, 27.13, 26.58, 25.12, 20.79, 19.74.

MS (EI): 311 (13.40), 293 (3.65), 269 (75.76), 237 (60.40), 219 (25.13), 205 (100), 191 (17.62), 177 (14.83), 145 (24.59).

HR-MS (ESI): Calculated $C_{18}H_{30}O_6$ [M+H]⁺: 343.21152, found: 343.21113.

Examples 1-5: Preparation of Trialkyl Cyclohexane-1,2,4-tripropionates According to the Invention In a distillation apparatus comprising immersed tube, thermometer and a Raschig ring column with condenser attached, the amount me of trimethyl cyclohexane-1,2,4-tripropionate was initially charged and suspended in the amount ma of the alcohol. The apparatus was purged with nitrogen (6 l/h) through the immersed tube for at least one hour, before 0.15% by mass of tetra-"butyl titanate (Sigma Aldrich, purity >97%), based on the mass of tripropionate, was added. While sparging with nitrogen (6 l/h), which lasts until the end of the reaction, the mixture was slowly heated to boiling while stirring. From 61 to 63° C. top temperature, methanol was produced which was continuously removed from the reaction via the distillation head. If the top temperature exceeded 68° C., no distillate was removed. In the course of the transesterification, an amount mm of methanol was produced (reaction time t). Hourly samples were taken during the reaction and these were analyzed by gas chromatography. If less than 0.5 area % of the monomethyl ester could be detected in the GC analysis, the heating medium was removed and the content of the reaction flask was cooled to 80° C. with introduction of nitrogen.

For processing, the crude product was transferred to a distillation apparatus with Claisen adapter and vacuum divider. Under reduced pressure (ca. 1 mbar) and at ca. 160° C. or ca. 180° C. bottom temperature (tributyl and tripentyl esters ca. 160° C., tri(2-ethylhexyl) ester and tri($^{iso}$nonyl) ester ca. 180° C.), the excess alcohol was distilled off and the mixture subsequently cooled again under a nitrogen atmosphere. The acid number of the contents of the flask was determined and then, with nitrogen sparging (6 l/h), the contents were stirred with a threefold stoichiometric amount of base (10% aqueous NaOH solution, NaOH from Merck, purity >99%) at 80° C. for 15 min. Subsequently, 2% by weight activated carbon (Cabot Norit Nederland B. V., CAP Super), based on the mass of the flask contents, were filled therein and stirred for 5 minutes. The remaining volatile fractions were once again removed under vacuum and at ca. 160° C. or ca. 180° C. (see above) with the aid of a nitrogen inlet, in which the nitrogen stream was adjusted so that the pressure did not exceed 20 mbar. If the residual alcohol content according to GC analysis was less than 0.025 area %, the resulting crude product was cooled and filtered through a Buchner funnel with filter paper and precompacted filter cake of filtration aid (Perlite type D14) into a suction bottle by means of reduced pressure.

The amount $m_p$ of the respective trialkyl cyclohexane-1,2,4-tripropionate (Tc ester) was obtained with the purity specified (%) in Table 1.

Particular Features of the Individual Syntheses:

In the preparation of the tri(2-ethylhexyl) ester, of the tri($^{iso}$nonyl) ester and of the tri(2-propylheptyl) ester, in the course of the transesterification (at 240° C. bottom temperature) reduced pressure was applied in a stepwise manner while maintaining reflux. In this case, the top temperature dropped slowly with reducing pressure.

TABLE 1

Details for preparing trialkyl cyclohexane-1,2,4-tripropionates according to the invention

| Ex. | $m_e$ (Tc-Ester) [g]/[mol] | Alcohol | $m_a$ (alcohol) [g]/[mol] | $m_m$ (MeOH) [g]/[mol] | Reaction time t [h] | $m_p$/Yield/Purity by GC [g]/[%]/[%] |
|---|---|---|---|---|---|---|
|  | 171/0.5 |  | 139/1.88 | 48/1.5 | 6 | 158/67/98.1 |
| 2* | 514/1.5 |  | 496/5.6 | 144/4.5 | 3.5 | 617/81/98.0 |
| 3* | 190/0.55 | 2-Ethylhexanol | 269/2.1 | 53/1.65 | 2.5 | 275/78/98.3 |
| 4* | 190/0.55 |  | 297/2.1 | 53/1.65 | 2.5 | 267/71/98.6 |
| 5* | 240/0.7 | 2-Propylheptanol | 415/2.6 | 67/2.1 | 8 | 440/87/98.1 |

*inventive
"Butanol: Sigma Aldrich, purity >99.4%
$^{iso}$Pentanol: mixture of "pentanol (Sigma Aldrich, purity >99%) and 2-methylbutanol (Sigma Aldrich, purity >99%) in a 1:1 molar ratio)
2-Ethylhexanol: Sigma Aldrich, purity >99%
Evonik Performance Materials GmbH, purity >99%
Evonik Performance Materials GmbH, purity >99.5%

Examples 6-10: Preparation of Non-Inventive Trialkyl Cyclohexane-1,2,4-tricarboxylates In a distillation apparatus comprising immersed tube, thermometer and a condenser with water separator attached, the amount $m_s$ of cyclohexane-1,2,4-tricarboxylic acid (Ct acid, >97%) was initially charged and suspended in the amount ma of the alcohol. The apparatus was purged with nitrogen (6 l/h) through the immersed tube for at least one hour, before 0.15% by mass of tetra-"butyl titanate (Sigma Aldrich, purity >97%), based on the mass of cyclohexane-1,2,4-tricarboxylic acid, was added. While sparging with nitrogen (6 l/h), which lasts until the end of the reaction, the mixture was slowly heated to boiling while stirring. The resulting water of reaction was removed continuously from the reaction via the water separator. If continuous reflux was no longer present, cyclohexane was added in an amount mc as azeotroping agent. In the course of the esterification, an amount mw of water was produced (reaction time t). After reaching the theoretical amount of water of reaction, half-hourly samples were taken for determination of the acid number. If an acid number of <0.1 mg KOH/g was measured, the contents of the reaction flask were cooled to 80° C. by removing the heat source and introducing nitrogen.

For processing, the crude product was transferred to a distillation apparatus comprising Claisen adapter with vacuum divider. Under reduced pressure (ca. 1 mbar) at ca. 160° C. or ca. 180° C. bottom temperature (tri(n-butyl) ester and tri($^{iso}$pentyl) ester ca. 160° C., tri(2-ethylhexyl) ester, tri(isononyl) ester and tri(2-propylheptyl) ester ca. 180° C.), the excess alcohol was distilled off and the mixture subsequently cooled again under a nitrogen atmosphere. The acid number of the contents of the flask was determined and then, with nitrogen sparging (6 l/h), the contents were stirred with a threefold stoichiometric amount of base (10% aqueous NaOH solution, NaOH from Merck, purity >99%) at 80° C. for 15 min. Subsequently, 2% by weight activated carbon (Cabot Norit Nederland B. V., CAP Super), based on the mass of the flask contents, were filled therein and stirred for 5 minutes. The remaining volatile fractions were once again removed under vacuum at ca. 160° C. or ca. 180° C. (see above) with the aid of a nitrogen inlet, in which the nitrogen stream was adjusted so that the pressure did not exceed 20 mbar. If the residual alcohol content according to GC analysis was less than 0.025 area %, the resulting crude product was cooled and filtered through a Buchner funnel with filter paper and precompacted filter cake of filtration aid (Perlite type D14) into a suction bottle by means of reduced pressure.

The amount $m_p$ of the respective trialkyl cyclohexane-1,2,4-tricarbxylate was obtained with the purity in percent (%) specified in Table 2.

Particular Features of the Individual Syntheses:

Preparation of the tri($^n$butyl) ester: In this experiment, 0.15% by weight sulfuric acid (Sigma-Aldrich, purity 95-97%), based on the mass of cyclohexane-1,2,4-tricarboxylic acid, was added together with tetra-$^n$butyl titanate. In addition, the contents of the reaction flask were cooled to 80° C. by introducing nitrogen if an acid number of <1 mg KOH/g (instead of <0.1 mg KOH/g) was measured.

Preparation of the tri($^n$butyl) ester and the tri($^{iso}$pentyl) ester: At the start of the reaction, only half the amount of tetra-$^n$butyl titanate described above and of the respective alcohol was initially charged and the residual amount was added only on reaching a bottom temperature of 240° C.

TABLE 2

Details for preparing non-inventive trialkyl cyclohexane-1,2,4-tricarboxylic esters (Ct-Ester)

| Ex. | $m_s$ (Ct-acid) [g]/[mol] | Alcohol | $m_a$ (alcohol) [g]/[mol] | $m_w$ (H$_2$O) [g]/[mol] | Reaction time t/$m_c$ (cyclohexane) [h]/[mL] | Yield/purity by GC [g]/[%]/[% R] |
|---|---|---|---|---|---|---|
| 6 | 184/0.85 | $^n$-Butanol: | 217/2.9 | 46/2.6 | 16/120 | 240/74/99.2 |
| 7 | 432/2 |  | 563/7.5 | 108/6 | 7/0 | 583/68/99.0 |
| 8 | 184/0.85 | 2-Ethylhexanol | 382/2.9 | 46/2.6 | 3/30 | 339/72/99.1 |
| 9 | 184/0.85 |  | 422/2.9 | 46/2.6 | 2.5/50 | 353/70/99.5 |
| 10 | 162/0.75 | 2-Propylheptanol | 409/2.6 | 41/2.3 | 2.5/25 | 332/69/99.4 |

$^n$-Butanol: Sigma Adrich, purity >99.4%
$^{iso}$Pentanol: mixture of $^n$pentanol (Sigma Aldrich, purity >99%) and 2-methylbutanol (Sigma Aldrich, purity >99%) in a 1:1 molar ratio
2-Ethylhexanol: Sigma Aldrich, purity >99%
$^{iso}$Nonanol: Evonik Performance Materials GmbH, purity >99%
2-Propylheptanol: Evonik Performance Materials GmbH, purity >99.5

Example 11: Intrinsic Viscosity of the Esters of Examples 1 to 10

The viscosity was determined by means of a Stabinger viscometer (SVM3000 from Anton Paar), which is a modification of the classical Couette rotational viscometer. The esters were injected individually and bubble-free into the measuring cell according to the instruction manual and measured at 20° C.

The intrinsic viscosities of the esters are listed in Table 3.

TABLE 3

Intrinsic viscosity of the esters of Examples 1 to 10 at 20° C. [mPa · s]

| | Trialkyl cyclohexane-1,2,4-tripropionate* | Trialkyl cyclohexane-1,2,4-tricarboxylate |
|---|---|---|
| $^n$butyl | 52.3 | 47.4 |
| | 79.7 | 69.1 |
| | 151.8 | 158.0 |
| | 168.0 | 163.5 |
| | 217.5 | 222.9 |

*inventive

Example 12: Production of Plastisols

PVC plastisols were produced, as used, for example, for the manufacture of topcoat films for floor coverings. The figures in the plastisol formulations are each in parts by mass. The formulations of the polymer compositions are listed in Table 4.

TABLE 4

Plastisol formulation

| | |
|---|---|
| PVC (Vestolit B 7021-Ultra; from Vestolit) | 100 |
| Triester (mixture) of Example 1*, 2*, 3*, 6, 7 or 8 | 50 |
| Epoxidized soybean oil as costabilizer (Drapex 39, from Galata) | 3 |
| Thermal stabilizer based on Ca/Zn (Reagent CLX/759/6PF) | 2 |

Figures in phr (phr = parts per hundred parts resin)

First the liquid constituents and then the pulverulent constituents were weighed out into a PE beaker. The mixture was stirred manually with an ointment spatula in such a way that no unwetted powder was present any longer. The mixing beaker was then clamped into the clamping device of a dissolver stirrer. After switching on the stirrer, the speed was slowly increased to ca. 2000 rpm (revolutions per minute). Meanwhile, the plastisol was carefully deaerated, the pressure being kept below 20 mbar. As soon as the plastisol had reached a temperature of ca. 30° C., the speed was lowered to ca. 350 rpm. Henceforth, the plastisol was deaerated for 9 minutes at this speed and a pressure below 20 mbar. This ensured that the plastisol was homogenized with a defined energy input. Thereafter, the plastisol was immediately equilibrated to 25.0° C. in a climate-controlled cabinet for further studies.

Example 13: Determination of the Thickening Behavior

The viscosities of the plastisols produced in Example 12 were measured with a Physica MCR 101 rheometer (Anton Paar Germany GmbH) with the aid of the associated software, using the rotation mode and the CC27 measuring system.

The following points were controlled during the measurement.
- a pre-shear of 100 $s^{-1}$ for a period of 60 s, during which no measurements were taken,
- shear rate downward progression from 200 $s^{-1}$ to 0.1 $s^{-1}$. 30 measurement points were taken each with a measurement point duration of 10 seconds.

The measurements were carried out after storage for 2 hours, 24 hours and 7 days. The plastisols were stored at 25° C. between measurements.

The thickening behavior of the plastisols was determined at a shear rate of 1, 10 and 100 $s^{-1}$ by means of the percentage viscosity increase after 24 hours and after 7 days, based on the viscosity value after 2 hours.

TABLE 5

Thickening behavior of the plastisols of Example 12 at 1 $s^{-1}$

| | Viscosity [Pa · s] after 2 h | Viscosity [Pa · s] after 24 h | Thickening [%] after 24 h | Viscosity [Pa · s] after 7 days | Thickening [%] after 7 days |
|---|---|---|---|---|---|
| Trialkyl cyclohexane-1,2,4-tripropionate | 2.53 | 3.3 | 30.4 | 4.77 | 88.5 |
| | 2.64 | 3.15 | 19.3 | 3.97 | 50.4 |
| | 3.15 | 3.36 | 6.7 | 3.66 | 16.2 |
| Trialkyl ″butyl cyclohexane-1,2,4-tricarboxylate | 6.23 | 11.2 | 79.8 | 26.5 | 325.4 |
| | 3.62 | 5.04 | 39.2 | 7.63 | 110.8 |
| | 3.92 | 4.44 | 13.3 | 5.28 | 34.7 |

* according to the invention

TABLE 6

Thickening behavior of the plastisols of Example 12 at 10 $s^{-1}$

| | Viscosity [Pa · s] after 2 h | Viscosity [Pa · s] after 24 h | Thickening [%] after 24 h | Viscosity [Pa · s] after 7 days | Thickening [%] after 7 days |
|---|---|---|---|---|---|
| Trialkyl cyclohexane-1,2,4-tripropionate | 2.28 | 2.94 | 28.9 | 4.11 | 80.3 |
| | 2.51 | 2.99 | 19.1 | 3.71 | 47.8 |
| | 3.26 | 3.47 | 6.4 | 3.76 | 15.3 |
| Trialkyl ″butyl cyclohexane-1,2,4-tricarboxylate | 5.44 | 9.42 | 73.2 | 20.9 | 284.2 |
| | 3.32 | 4.37 | 31.6 | 6.36 | 91.6 |
| | 4.05 | 4.52 | 11.6 | 5.27 | 30.1 |

* according to the invention

TABLE 7

Thickening behavior of the plastisols of Example 12 at 100 $s^{-1}$

| | Viscosity [Pa · s] after 2 h | Viscosity [Pa · s] after 24 h | Thickening [%] after 24 h | Viscosity [Pa · s] after 7 days | Thickening [%] after 7 days |
|---|---|---|---|---|---|
| Trialkyl cyclohexane-1,2,4-tripropionate | 3.11 | 3.98 | 28 | 5.41 | 74 |
| | 3.7 | 4.34 | 17.3 | 5.27 | 42.4 |
| | 5.77 | 5.92 | 2.6 | 6.19 | 7.3 |

TABLE 7-continued

Thickening behavior of the plastisols of Example 12 at 100 s$^{-1}$

| | | Viscosity [Pa · s] after 2 h | Viscosity [Pa · s] after 24 h | Thickening [%] | Viscosity [Pa · s] after 7 days | Thickening [%] |
|---|---|---|---|---|---|---|
| Trialkyl cyclohexane-1,2,4-tricarboxylate | $^n$butyl | 6.71 | 10.8 | 61 | 21 | 213 |
| | | 4.66 | 5.88 | 26.2 | 8.1 | 73.8 |
| | | 6.61 | 7.09 | 7.3 | 7.97 | 20.6 |

* according to the invention

The plastisol viscosity of trialkyl cyclohexane-1,2,4-tripropionates according to the invention is lower than the plastisol viscosity of the comparative esters. In addition, the increase in viscosity of the trialkyl cyclohexane-1,2,4-tripropionates with time is less pronounced than in the comparative esters. By virtue of these advantageous properties, the triesters according to the invention can be used even after longer standing without addition of viscosity-lowering additives which, besides the use of these additives, also saves time and effort associated with their use.

Example 14: Preparation of Films

The plastisols prepared in Example 12 were each processed to give films 1 mm thick.

For this purpose, first of all high-gloss release paper (from Sappi, Italy) was trimmed to a size of 30×44 cm and inserted in the clamping frame of the LTSV coating installation for the Mathis oven. The clamping frame was subsequently placed on the guide frame, the Mathis oven (model LTF) was adjusted to 200° C., and on reaching this temperature, the frame was preheated for 15 seconds. The knife coater was subsequently inserted into the clamping means and the knife gap was adjusted via preliminary experiments in such a way that the film thickness after the end of gelling was 1 mm (+/−0.05 mm). An adhesive strip was mounted on the leading edge of the paper in order to catch excess plastisol. The plastisol was then applied in front of the coating knife, and spread by drawing of the guide frame with the coating knife over the clamped released paper (at a speed of 3 m/min). The coating knife was then removed and the adhesive strip with the excess plastisol was removed. The clamping frame was then moved into the oven. After gelling had taken place (2 minutes at 200° C.), the frame was moved out of the oven again and, after cooling, the film was removed from the paper.

Example 15: Mass Loss of the Films

Each of 6 dumbbell specimens (type S2 in accordance with DIN 53504) per formulation from Example 14 was conditioned overnight under a standard climate (23° C., 50% relative humidity) and subsequently weighed. Subsequently, the dumbbell specimens were stored at 80° C. suspended in a convection-operated heating cabinet over a tray (28×20×6 cm) filled with activated carbon at a minimum gap of 20 mm. After 7 or 14 days, the dumbbell specimens were removed, stored overnight in a dessicator and subsequently weighed. The mass loss was determined by subtraction for each individual dumbbell specimen. The average values in percent for the mass loss of each of six individual measurements per formulation are stated in Table 8.

TABLE 8

Mass loss of films in air (80° C.)

| | Trialkyl cyclohexane-1,2,4-tripropionate* | | Trialkyl cyclohexane-1,2,4-tricarboxylate | |
|---|---|---|---|---|
| | after 7 d | after 14 d | after 7 d | after 14 d |
| $^n$butyl | 0.8% | 0.9% | 3.4% | 6.1% |
| | 0.7% | 0.8% | 1.5% | 2.4% |
| | 0.6% | 0.7% | 0.8% | 0.9% |

*inventive

The mass loss of films comprising triesters according to the invention is lower than that of films comprising the corresponding trialkyl cyclohexane-1,2,4-tricarboxylates.

Example 16: Glass Transition Temperatures of the Films

The glass transition temperature was determined by DMTA measurements in accordance with DIN 65583 using a type MCR 302 rheometer from Anton Paar. Under constant dynamic mechanical conditions (1 Hz, deformation 0.3%), the viscoelastic properties of the films were recorded as a function of temperature (temperature ramp from −100 to +50° C.) and the storage modulus, the loss modulus and the loss factor were determined. The maximum of the loss modulus is interpreted in this case as the glass transition temperature. The following Table shows in each case the average value of a duplicate determination.

TABLE 9

Glass transition temperatures $T_g$ of the films in ° C.

| | Trialkyl cyclohexane-1,2,4-tripropionate* | Trialkyl cyclohexane-1,2,4-tricarboxylate |
|---|---|---|
| $^n$butyl | −27 | −15 |
| | −28 | −18 |
| | −37 | −24 |

*inventive

As evident from the lower glass transition temperatures, the low temperature flexibility in esters according to the invention is distinctly improved compared to the comparative compounds.

Example 17: Production of Dryblends, Rolled Sheets and Pressed Plaques

The test specimens required for the examples which follow are produced by dry mixing (dryblend production), calendering (rolling) and pressing of the following formulations:

TABLE 10

| Dryblend formulation | |
| --- | --- |
| PVC (Inovyn 271 PC; from Inovyn) | 100 |
| Triester (mixture) of Example 3*, 4*, 5*, 8, 9, 10 Tri(2-ethylhexyl) trimellitate or tri($^{iso}$nonyl) trimellitate | 50 |
| Chalk filler (OMYA BSH) | 20 |
| Thermal stabilizer (Baeropan MC 8890/KA/2/MC) | 10 | phr: (phr = parts per hundred parts resin)
Tri(2-ethylhexyl) trimellitate: Eastman Chemical Company, purity > 99%
Tri($^{iso}$nonyl) trimellitate: UPC Technology, Taiwan, purity > 98%

With dry mixtures, which are referred to as dryblends, it is possible, for example, after thermoplastic processing (e.g. calendering or extrusion) to produce cable and wire insulation, hoses or floors and roofing membranes.

The dryblends were produced in a Brabender planetary mixer.

The "Winmix" software was used to set the following parameters in the Brabender planetary mixer:
Speed program: active
Profile: speed 50 rpm; hold time: 9 min;
  Rise time (of the speed): 1 min;
  speed 100 rpm; hold time: 20 min
Temperature: 88° C.
Measurement range: 2 Nm
Damping: 3

The temperature in the mixing vessel was 88° C. after one-hour equilibration period. Once the planetary mixer had conducted an internal calibration, the solid constituents (PVC, stabilizer), which had been weighed out beforehand in four times the amount (four times the amount in g based on Table 10 in phr) into a PE beaker on an analytical balance, were fed to the mixing vessel via a solids funnel and the filling stub present in the Brabender mixing vessel. The program was started and the powder mixture was stirred and equilibrated in the mixing vessel for 9 minutes, before the liquid constituents, which had likewise been weighed out in four times the amount in a PE beaker on the balance, were fed in via a liquid funnel and the filling stub present in the Brabender mixing vessel. The mixture was stirred in the planetary mixer for a further 20 minutes. After the program had ended, the finished dry mixture (dryblend) was removed.

These dryblends were used to produce rolled sheets. The rolled sheets were produced on a Collin W150 AP calender. The Collin calender has an automatic sample turner and its temperature is controlled by means of an additional oil thermostat. Control was effected by means of Collin software.

A five-stage program was used to produce the rolled sheet:

| Stage | Designation | Temp. [° C.] | Duration m (STP)/s | Gap width MAmt | Speed [rpm] |
| --- | --- | --- | --- | --- | --- |
| 1 | Plastification of the dryblend | 165 | 60 | 0.2 | 5 |
| 2 | Increasing the gap size | 165 | 30 | 0.5 | 20 |
| 3 | Activation of the sample turner | 165 | 170 | 0.5 | 20 |
| 4 | Rolled sheet optimization | 165 | 30 | 0.5 | 25 |
| 5 | Rolled sheet removal | 165 | 60 | 0.5 | 7 |

On attainment of the roll temperature, the roll gap was calibrated. To start the measurement, the roll gap was adjusted to 0.2 mm. 160 g of each dryblend were weighed in and introduced into the roll gap with the rollers stationary. The program was started.

The pressed plaques were produced with a Collin laboratory press. The prefabricated rolled sheets (see above) were used to produce the pressed plaques. The lateral edges of the rolled sheets were removed with the aid of a cutting machine, then the rolled sheet was cut into pieces of about 14.5×14.5 cm in size. For pressed plaques of thickness 1 mm, 2 rolled sheet pieces in each case were placed one on top of the other into the stainless steel pressing frame of size 15×15 cm.

A three-stage program was used to produce the pressed plaques:

| Stage | Designation | Pressure [bar] | Duration [s] |
| --- | --- | --- | --- |
| 1 | Initial pressing | 170 | 5 | 60 |
| 2 | Pressing | 170 | 200 | 200 |
| 3 | Cooling | 40 | 200 | 200 |

Example 18: Glass Transition Temperature of the Pressed Plaques

The glass transition temperature was determined by DMTA measurements in accordance with DIN 65583 using a type MCR 302 rheometer from Anton Paar. Under constant dynamic mechanical conditions (1 Hz, deformation 0.3%), the viscoelastic properties of the films were recorded as a function of temperature (temperature ramp from −100 to +50° C.) and the storage modulus, the loss modulus and the loss factor were determined. The maximum of the loss modulus is interpreted in this case as the glass transition temperature. The following Table shows in each case the average value of a duplicate determination.

TABLE 11

Glass transition temperatures $T_g$ of the pressed plaques in ° C.

| | Trialkyl cyclohexane-1,2,4-tripropionate* | Trialkyl cyclohexane-1,2,4-tricarboxylate | trialkyl trimellitate |
| --- | --- | --- | --- |
| 2-Ethylhexyl esters | −31 | −16 | −18 |
| $^{iso}$-Nonyl esters | −38 | −24 | −27 |
| | −57 | −35 | — |

*inventive

As evident from the lower glass transition temperatures, the low temperature flexibility in esters according to the invention is higher than in the comparative compounds. Good low temperature flexibility is particularly relevant for outdoor applications.

Example 19: Mass Loss of the Pressed Plaques

From the pressed plaques of Example 17, 6 test pieces each per formulation in the form of tensile specimens of the S2 type were punched out, conditioned overnight in a dessicator and subsequently weighed. Subsequently, the test specimens were stored at 135° C. suspended in a convection-operated heating cabinet over a tray (28×20×6 cm) filled with activated carbon at a minimum gap of 20 mm. After 14 days, the test specimens were removed, stored overnight under a standard climate and subsequently weighed. The difference of the masses determined for the respective test specimens is the mass loss. The average values in percent of each of three individual measurements per formulation are stated in Table 12.

TABLE 12

Mass loss of pressed plaques in air
(after 14 days' storage at 135° C.) in mass %

|  | Trialkyl cyclohexane-1,2,4-tripropionate* | Trialkyl cyclohexane-1,2,4-tricarboxylate | trialkyl trimellitate |
|---|---|---|---|
| 2-Ethylhexyl esters | −1.7 | −11.5 | −7 |
| $^{iso}$Nonyl esters | −1.3 | −2.9 | −1.8 |
| 2-Propylheptyl esters | −1.7 | −2.4 | — |

*inventive

The mass loss of pressed plaques comprising triesters according to the invention is lower than that of films comprising the corresponding trialkyl cyclohexane-1,2,4-tricarboxylates or the corresponding trialkyl trimellitates.

The invention claimed is:

1. A composition comprising
   a triester of cyclohexanetripropionic acid wherein the ester comprises a propionic acid moiety and an alcohol moiety wherein the three alcohol moieties of the three ester groups each 5 to 12 carbon atoms, wherein the alcohol moieties have identical carbon atom number within one molecule: and
   one or more polymers.

2. The composition according to claim 1, wherein the triester of cyclohexanetripropionic acid is a triester of cyclohexane-1,2,4-tripropionic acid or a triester of cyclohexane-1,3,5-tripropionic acid, and wherein the three alcohol moieties of the three ester groups each comprise 7 to 12 carbon atoms.

3. The composition according to claim 1, wherein the alcohol moieties, besides the oxygen of the ester function, do not comprise any other heteroatoms, and contain no multiple bonds.

4. The composition according to claim 1, wherein all alcohol moieties present in one molecule have identical empirical formulae and at the same time identical or different structural formulae.

5. The composition according to claim 2, wherein the triester of cyclohexanetripropionic acid is selected from the group consisting of:
   tri($^n$pentyl) cyclohexane-1,2,4-tripropionate, tri($^{iso}$pentyl) cyclohexane-1,2,4-tripropionate, tri(2-methylbutyl) cyclohexane-1,2,4-tripropionate, tri(3-methylbutyl) cyclohexane-1,2,4-tripropionate, tri($^n$hexyl) cyclohexane-1,2,4-tripropionate, tri($^{iso}$hexyl) cyclohexane-1,2,4-tripropionate, tri($^n$heptyl) cyclohexane-1,2,4-tripropionate, tri($^{iso}$heptyl) cyclohexane-1,2,4-tripropionate, tri($^n$octyl) cyclohexane-1,2,4-tripropionate, tri($^{iso}$octyl) cyclohexane-1,2,4-tripropionate, tri(2-ethylhexyl) cyclohexane-1,2,4-tripropionate, tri($^n$nonyl) cyclohexane-1,2,4-tripropionate, tri($^{iso}$nonyl) cyclohexane-1,2,4-tripropionate, tri($^n$decyl) cyclohexane-1,2,4-tripropionate, tri($^{iso}$decyl) cyclohexane-1,2,4-tripropionate, tri(2-propylheptyl) cyclohexane-1,2,4-tripropionate,
   tri($^n$pentyl) cyclohexane-1,3,5-tripropionate, tri($^{iso}$pentyl) cyclohexane-1,3,5-tripropionate, tri(2-methylbutyl) cyclohexane-1,3,5-tripropionate, tri(3-methylbutyl) cyclohexane-1,3,5-tripropionate, tri($^n$hexyl) cyclohexane-1,3,5-tripropionate, tri($^{iso}$hexyl) cyclohexane-1,3,5-tripropionate, tri($^n$heptyl) cyclohexane-1,3,5-tripropionate, tri($^{iso}$heptyl) cyclohexane-1,3,5-tripropionate, tri($^n$octyl) cyclohexane-1,3,5-tripropionate, tri($^{iso}$octyl) cyclohexane-1,3,5-tripropionate, tri(2-ethylhexyl) cyclohexane-1,3,5-tripropionate, tri($^n$nonyl) cyclohexane-1,3,5-tripropionate, tri($^{iso}$nonyl) cyclohexane-1,3,5-tripropionate, tri($^n$decyl) cyclohexane-1,3,5-tripropionate, tri($^{iso}$decyl) cyclohexane-1,3,5-tripropionate and tri(2-propylheptyl) cyclohexane-1,3,5-tripropionate.

6. The composition according to claim 1, wherein at least one polymer is selected from the group consisting of polyvinyl chloride, polyalkyl methacrylate (PAMA), polyvinyl butyral (PVB), polyurethane, polysulfide, polylactic acid (PLA), polyhydroxybutyral (PHB), nitrocellulose and copolymers of vinyl chloride with vinyl acetate or with butyl acrylate.

7. The composition according to claim 1, wherein said composition is a constituent of an adhesive, of a sealing compound, of a coating composition, of a lacquer, of a paint, of a plastisol, of a dryblend, of a foam, of a synthetic leather, of a floor covering, the top layer or foam layer thereof, of a roofing membrane, of an underbody protection, of a fabric coating, of a cable, of a wire insulation, of a hose, of an extruded article, of a film, of an article in the automotive interior sector, of a wallpaper, of an ink, of a toy, of a contact sheet, of a food packaging or of a medical article.

8. The composition according to claim 2, wherein the alcohol moieties, besides the oxygen of the ester function, do not comprise any other heteroatoms, and contain no multiple bonds.

9. The composition according to claim 2, wherein all alcohol moieties present in one molecule have identical empirical formulae and at the same time identical or different structural formulae.

10. The composition according to claim 1, wherein the triester of cyclohexanetripropionic acid is a triester of cyclohexane-1,2,4-tripropionic acid or a triester of cyclohexane-1,3,5-tripropionic acid.

11. The composition according to claim 1, further comprising a mixture of at least two triesters of cyclohexanetripropionic acid.

12. The composition according to claim 11, wherein all alcohol moieties present in one molecule have identical empirical formulae and at the same time identical or different structural formulae.

13. The composition according to claim 11, wherein the alcohol moieties, besides the oxygen of the ester function, do not comprise any other heteroatoms, and contain no multiple bonds.

14. The composition according to claim 6, wherein the triester of cyclohexanetripropionic acid is selected from the group consisting of:
   tri($^n$pentyl) cyclohexane-1,2,4-tripropionate, tri($^{iso}$pentyl) cyclohexane-1,2,4-tripropionate, tri(2-methylbutyl) cyclohexane-1,2,4-tripropionate, tri(3-methylbutyl) cyclohexane-1,2,4-tripropionate, tri($^n$hexyl) cyclohexane-1,2,4-tripropionate, tri($^{iso}$hexyl) cyclohexane-1,2,4-tripropionate, tri($^n$heptyl) cyclohexane-1,2,4-tripropionate, tri($^{iso}$heptyl) cyclohexane-1,2,4-tripropionate, tri($^n$octyl) cyclohexane-1,2,4-tripropionate, tri($^{iso}$octyl) cyclohexane-1,2,4-tripropionate, tri(2-ethylhexyl) cyclohexane-1,2,4- tripropionate, tri($^n$nonyl) cyclohexane-1,2,4-tripropionate, tri($^{iso}$nonyl) cyclohexane-1,2,4-tripropionate, tri($^n$decyl) cyclohexane-1,2,4-tripropionate, tri($^{iso}$decyl) cyclohexane-1,2,4-tripropionate, tri(2-propylheptyl) cyclohexane-1,2,4-tripropionate, tri($^n$pentyl) cyclohexane-1,3,5-tripropionate, tri($^{iso}$pentyl) cyclohexane-1,3,5-tripropionate, tri(2-methylbutyl) cyclohexane-1,3,5-tripropionate, tri(3-methylbutyl) cyclohexane-1,3,5-tripropionate, tri($^n$hexyl) cyclohexane-1,3,5-tripropionate, tri($^{iso}$hexyl) cyclohexane-1,3,5-tripropionate, tri($^n$heptyl) cyclohexane-1,3,5-tripropionate, tri($^{iso}$heptyl) cyclohexane-1,3,5-tripropionate, tri($^n$octyl) cyclohexane-1,3,5-tripropionate, tri($^{iso}$octyl) cyclohexane-1,3,5-tripropionate, tri(2-ethylhexyl) cyclohexane-1,3,5-tripropionate, tri($^n$nonyl) cyclohexane-1,3,5-tripropionate, tri($^{iso}$nonyl) cyclohexane-1,3,5-tripropionate, tri($^n$decyl) cyclohexane-1,3,5-tripropionate, tri($^{iso}$decyl) cyclohexane-1,3,5-tripropionate and tri(2-propylheptyl) cyclohexane-1,3,5-tripropionate.

\* \* \* \* \*